(12) United States Patent
Wong

(10) Patent No.: US 7,083,929 B2
(45) Date of Patent: *Aug. 1, 2006

(54) PARALLEL POLYNUCLEOTIDE SEQUENCING METHOD

(75) Inventor: Wing H. Wong, Los Angeles, CA (US)

(73) Assignee: The Chinese University of Hong Kong, Shantin (HK)

( * ) Notice: Subject to any disclaimer, the term of this patent is extended or adjusted under 35 U.S.C. 154(b) by 331 days.

This patent is subject to a terminal disclaimer.

(21) Appl. No.: 10/627,465

(22) Filed: Jul. 25, 2003

(65) Prior Publication Data

US 2004/0029165 A1    Feb. 12, 2004

Related U.S. Application Data

(63) Continuation of application No. 09/371,265, filed on Aug. 10, 1999, now abandoned, which is a continuation of application No. 08/938,565, filed on Sep. 26, 1997, now Pat. No. 5,935,793.

(60) Provisional application No. 60/026,797, filed on Sep. 27, 1996.

(51) Int. Cl.
    *C12Q 1/68*    (2006.01)
    *C12P 19/34*   (2006.01)
    *C07H 21/04*   (2006.01)

(52) U.S. Cl. .................. 435/6; 435/91.1; 435/91.2; 536/24.33

(58) Field of Classification Search .............. 435/6, 435/91.1, 91.2; 536/23.1, 24.33
See application file for complete search history.

(56) References Cited

U.S. PATENT DOCUMENTS

| | | | |
|---|---|---|---|
| 4,942,124 A | 7/1990 | Church | 435/6 |
| 5,126,025 A | 6/1992 | Carson | 204/180.1 |
| 5,149,625 A | 9/1992 | Church et al. | |
| 5,695,934 A | 12/1997 | Brenner | 435/6 |

FOREIGN PATENT DOCUMENTS

| | | |
|---|---|---|
| EP | 0497448 A1 | 8/1992 |
| WO | WO 90/10718 | 9/1990 |
| WO | WO 96/12039 | 4/1996 |
| WO | WO 96/36737 | 11/1996 |
| WO | WO 97/18328 | 5/1997 |

OTHER PUBLICATIONS

International Search Report by Chinese Patent Office from related PCT Application No. PCT/IB97/01384.
Standard EPO Search Report from related PCT Application No. PCT/IB97/01384.

Beck, Stephen., "Nonradioactive Detection of DNA Using Dioxetane Chemiluminescence," Meth Enzymol. 216: 143-153 (1992).
Beck, Stephen., "Multiplex DNA Sequencing," Meth. Molec. Biol. 23: 225-234 (1993).
Chee, Mark, "Enzymatic multiplex DNA sequencing," Nucleic Acids Research. 19 (12) : 3301-3305 (1991).
Cherry, Joshua L., et al., "Enzyme-Linked Fluoescent Detection for Automated Multiplex DNA Sequencing," Genomics 20: 68-74 (1994).
Church, George M., and Stephen Kieffer-Higgins, "Multiplex DNA Sequencing," Science 240: 185-188 (1988).
Drmanac, R., et al., "DNA Sequence Determination by Hybridization: A Strategy for Efficient Large-Scale Sequencing," Science 260: 1649-1652 (1993).
Hensel, Michael., et al., "Simultaneous Identification of Bacterial Virulence Genes by Negative Selection," Science 269: 400-403 (1995).
Hunkapiller, T., et al., "Large-Scale and Automated DNA Sequence Determination," Science 254: 59-67 (1991).
Khrapko, K.R., et al., "A method for DNA sequencing by hybridization with oligonucleotide matrix," DNA Sequence 1: 375-388 (1991).
Richterich, P., and G.M. Church., "DNA Sequencing with Direct Transfer Electrophoresis and Nonradioactive Detection," Meth Enzymol. 218: 187-222 (1993).

*Primary Examiner*—Kenneth R. Horlick
(74) *Attorney, Agent, or Firm*—Townsend and Townsend and Crew LLP

(57) ABSTRACT

The invention is directed to a method for sequencing multiple target polynucleotide segments in parallel, and to compositions and kits therefor. In the method, a plurality of sample polynucleotide fragments are used to form a mixture of different-length sequencing fragments. The sequencing fragments are complementary to at least two different sample fragments, wherein (1) each sequencing fragment terminates at a predefined end with a known base or bases, and (2) each sequencing fragment contains an identifier tag sequence that identifies the sample fragment to which the sequencing fragment corresponds. The sequencing fragments are then separated on the basis of size to produce a plurality of resolved, size-separated bands. Resolved bands are collected in separate aliquots, which, in a preferred embodiment, are then subjected to an amplification step to amplify the complements of the tag sequences in each aliquot, and preferably, the tag sequences too. Amplification is preferably by PCR. The (amplified) aliquots are then separately hybridized with an array of immobilized different-sequence tag probes under conditions effective to provide specific hybridization of tag sequences, or of tag sequence complements, with the corresponding immobilized tag probes, to form a hybridization pattern on the array, from which sequence information of one or more sample fragments are determined.

13 Claims, 2 Drawing Sheets

PARALLEL POLYNUCLEOTIDE SEQUENCING METHOD

This application is a continuation of U.S. application Ser. No. 09/371,265, filed Aug. 10, 1999, now abandoned, which is a continuation of and claims priority under 35 U.S.C. §120 and §119 (e), as appropriate, to utility patent application Ser. No. 08/938,565 filed Sep. 26, 1997, now U.S. Pat. No. 5,935,793 issued Aug. 10, 1999, and to provisional application Ser. No. 60/026,797 filed Sep. 27, 1996, which are incorporated herein by reference in their entirety.

FIELD OF THE INVENTION

The present invention relates to a method of sequencing multiple target polynucleotide segments in parallel, and to compositions and kits therefor.

REFERENCES

Agrawal, S., et al., PCT Pub. WO 92/08728 (1992).
Albretsen et al., *Anal. Biochem.* 189:40 (1990).
Ansorge, W., et al., *J. Biochem. Biophys. Meth.* 13:315 (1986).
Ausubel, et al., Eds., *Current Protocols in Molecular Biology*, Greene & Wiley Interscience, New York, 1995).
Bains, W., et al., *J. Theor. Biol.* 135:303 (1988).
Barany, F., et al. PCT App. No. PCT/US91/06013 (1991).
Barrett, R. W., et al., U.S. Pat. No. 5,482,867 (1996).
Beaucage, S. L., et al., *Tetrahedron* 48:2223 (1992).
Bergot et al., PCT Pub. No. WO 90/05565 (1990).
Bergot et al., PCT Pub. No. WO 91/05060 (1991).
Breslauer et al., *Proc. Natl. Acad. Sci.* 83:3746 (1986).
Carson, W. W., et al., U.S. Pat. No. 5,126,025 (1992).
Caruthers, M., et al., PCT Pub. No. WO 89/11486 (1989).
Church, G. M., and Kieffer-Higgins, S., *Science* 240:185 (1988).
Church, G. M., U.S. Pat. No. 4,942,124 (1990).
Cruickshank, U.S. Pat. No. 5,091,519 (1992).
Drmanac, R., et al., *Electrophoresis* 13:566 (1992).
Drmanac, R., et al., *Science* 260:1649 (1993).
Eckstein, F., Ed., *Oligonucleotides and Analogues: A Practical Approach*, IRL Press, Oxford (1991).
Fleischmann, R. D., et al., *Science* 269:496 (1995).
Fodor, S. P. A., et al., Science 251:767 (1991).
Fodor, S. P. A., et al., U.S. Pat. No. 5,445,934 (1995).
Gait, M. J., *Oligonucleotide Synthesis*, IRL Press, Oxford (1990).
Grossman, P. D., U.S. Pat. No. 5,374,527 (1994).
Hanvey et al., *Science* 258:1481 (1992).
Haugland, *Handbook of Fluorescent Probes*, Molecular Probes Inc., Eugene, Oreg. (1992).
Hawkins, T. L., et al., *Science* 276:1887 (1997).
Heller, C., et al., *Gene* 103:131 (1991).
Huang, X. C., et al., *Anal. Chem.* 64:2149 (1992).
Jablonski et al., *Nucl. Acids. Res.* 14:6115 (1986).
Johnston, R. F., et al., *Electrophoresis* 11:355 (1990).
Ju, J., et al., *Proc. Natl. Acad. Sci.* 92:4347 (1995).
Lee, L., et al., *Nucl. Acids Res.* 20:2471 (1992).
Keller and Manak, DNA Probes, 2nd Ed., Stockton Press, New York, (1993).
Khrapko, K. R., et al., *DNA Sequencing* 1:375 (1991).
Kornberg and Baker, *DNA Replication,* 2nd Ed., Freeman Publishing, San Francisco (1992).
Lowe et al., *Nucl. Acids Res.* 18:1757 (1990).
Macevicz, S., PCT Application No. US89/04741.
Mathies, R. A., et al., U.S. Pat. No. 5,091,652 (1992).
Matthews et al., *Anal. Biochem.* 169:1 (1988).
Maxam, A. M., and Gilbert, W., *Proc. Natl. Acad. Sci.* 74:560 (1977).
Menchen, S. M., et al., U.S. Pat. No. 5,188,934 (1993).
Menchen, S. M., et al., PCT Pub. No. WO 94/07133 (1994).
Mullis, K., U.S. Pat. No. 4,683,202 (1987).
Northrop, M. A., et al., *Transducers* '93 pp. 924-926, from The 7th Int'l Conference on Solid-State Sensors and Actuators (1993).
Pardee, A. B., et al., U.S. Pat. No. 5,262,311 (1993).
Ploem, J. S., in *Fluorescent and Luminescent Probes for Biological Activity*, Mason, T. W., Ed., Academic Press, London, pp. 1–11 (1993).
Pon et al., *Biotechniques*, 6:768 (1988).
Prober, J. M., *Science* 238:336 (1987).
Saiki, R. K., et al., *Science* 230:1350 (1985).
Sambrook et al., *Moleculer Cloning: A Laboratory Manual*, 2nd Ed., Cold Spring Harbor Laboratory, New York, 1989).
Sanger, F. and Coulson, A. R., *Proc. Natl. Acad. Sci.* 74:5463 (1977).
Scheit, *Nucleotide Analogs*, John Wiley Publishing, New York (1980).
Shalon, D., Ph.D. Dissertation, Falconer Library, Stanford University, California (1995).
Schena, M., et al., *Science* 270:467 (1995).
Smith, L. M., *Nature* 321:674 (1987).
Stec, W. J., et al., U.S. Pat. No. 5,359,052 (1994).
Strezoska, Z., et al., *Proc. Natl. Acad. Sci.* 88:10089 (1991).
Uhlman and Peyman, *Chem. Rev.* 90:543 (1990).
Urdea, M. S., U.S. Pat. No. 5,124,246 (1992).
Wetmur, *Critical Reviews in Biochemistry and Molecular Biology* 26:227 (1991).
Wilding, P., et al., *Clin. Chem.* 40:1815 (1994).
Wittwer, C. T., et al., *Anal. Biochem.* 186:328 (1990).
Wittwer, C. T., et al., *Biotechniques* 10:76 (1991).
Yershov, G., et al., *Proc. Natl. Acad. Sci.* 93:4913 (1996).

BACKGROUND

Increasing the speed of polynucleotide sequencing is at present one of the most pressing problems in molecular biology. Although sequencing speed has increased manyfold due to advances in labeling and detection (e.g., Smith, 1985; Ansorge, 1986), current automatic sequencing machines employ essentially the same principles as originally proposed in 1977 (Maxam, 1977; Sanger, 1977).

In the method of Maxam and Gilbert, a terminally labeled oligonucleotide is cleaved internally, in four separate reaction mixtures under partial cleavage conditions, using chemical reagents which cleave at one or two defined base-types. The truncated reaction products are resolved on the basis of size, and the oligonucleotide sequence is determined from the order of elution of the fragments, taking into account the base-specificities of the cleavage reagents.

The method of Sanger, on the other hand, involves enzymatic extension of a 5'-primer along a target template strand in the presence of the four standard deoxynucleotide bases, plus one base in dideoxy form. Random incorporation of the selected dideoxynucleotide results in a mixture of products of variable length, each terminating at its 3'-end with the dideoxynucleotide. As originally proposed, four sequencing reactions were performed for a given target sequence, one for each dideoxynucleotide base-type. The products from each mixture were then resolved in four separate lanes on the basis of size, and the target sequence was determined in a manner similar to that used in the Maxam and Gilbert method. Variants were later developed which use spectrally resolvable fluorescent dyes attached to either the 5'-extension primer (Smith, 1985) or the 3'-dideoxy terminator bases (Prober, 1987; Bergot, 1991), allowing determination of the target sequence using a single separation path.

In 1988, Church et al. proposed a "multiplex" sequencing method by which multiple sequences could be determined after coelution of sequencing fragments from different targets in a single gel lane. The separated fragments are transferred to a membrane and then iteratively hybridized with different template probes to obtain sequence data, one sequence at a time. Unfortunately, this method requires time-consuming probing and washing steps and is not efficient for large scale sequencing projects.

As an alternative to the methods above, a "sequencing by hybridization" approach was proposed wherein groups of consecutive bases are determined simultaneously through hybridization of a target sequence with a complete set of all possible sequences of length k (k-tuples) (e.g., Bains, 1988; Macevicz, 1989). In one approach, a sample polynucleotide is hybridized to a set of all possible k-tuple oligonucleotides immobilized as an ordered array (Macevicz, 1989). The pattern of hybridization on the array allows the sequence to be determined, albeit only for short sequences. In a second approach, multiple sample polynucleotides are immobilized as an ordered array on a support and are hybridized sequentially with a series of k-tuples (Strezoska, 1991). With this method, however, an enormous number of probing steps is required before meaningful sequence information for any of the sample polynucleotides can be obtained. Moreover, both sequence by hybridization approaches are inefficient in terms of the number of k-tuple probes used, most of which do not bind to the sample.

In view of the inadequacies of the methods proposed to date, there is a need for new sequencing methods which are capable of providing sequencing data for a large number of target sequences. Ideally, the number of time-consuming or expensive steps will remain relatively constant or increase slowly with the number of templates. In addition, the method should be amenable to automation, so that the involvement of manual steps is reduced.

SUMMARY OF THE INVENTION

The present invention includes a method of sequencing in parallel a plurality of polynucleotide sample fragments. In the method, a plurality of sample polynucleotide fragments is used to form a mixture of different-length sequencing fragments. The sequencing fragments are complementary to at least two different sample fragments, wherein (1) each sequencing fragment terminates at a predefined end with a known base or bases, and (2) each sequencing fragment contains an identifier tag sequence that identifies the sample fragment to which the sequencing fragment corresponds. The identifier tag sequences preferably have melting temperatures, with respect to their sequence complements, that are within a preselected temperature range. The sequencing fragments are then separated on the basis of size under conditions effective to resolve fragments differing in length by a single base, to produce a plurality of resolved, size-separated bands. Preferably, separation is accomplished by electrophoresis techniques, and more preferably, by capillary electrophoresis. During or after size-separation, the resolved bands are collected in separate aliquots, which are preferably subjected to an amplification step to amplify the complements of the tag sequences in each aliquot, and optionally, the tag sequences too. The fragment aliquots are then separately contacted with an array of immobilized different-sequence tag probes, each tag probe (1) being capable of hybridizing specifically with one of the identifier tag sequences or a tag sequence complement thereof, and (2) having an addressable location in the array. The contacting step is conducted under conditions effective to provide specific hybridization of tag sequences, or of tag sequence complements, with the corresponding immobilized tag probes, to form a hybridization pattern on the array. From the hybridization patterns formed on the arrays, a sequence is determined for at least one sample fragment.

In one embodiment, the method involves the use of tagged primers, each containing (i) an identifier tag sequence, and (ii) a first primer sequence located on the 3'-side of the tag sequence, for forming sequencing fragments having a unique identifier tag associated with each different-sequence sample fragment. Prior to hybridization with the tag-probe array, the tagged primer sequences are preferably amplified to form multiple copies of the corresponding tag-primer complements, and optionally, the tag sequences too, for hybridizing to the immobilized tag probes on the array.

In a preferred embodiment, the tag primers are amplifiable, and formation of the sequencing fragments includes the steps of (1) inserting the sample polynucleotide fragments into a plurality of identical vectors, to form a mixture of sequencing vectors, (2) isolating a plurality of unique-sequence clones from the sequencing vector mixture, (3) separately hybridizing to each unique-sequence clone, a tagged primer containing (i) an identifier tag sequence, and (ii) a first primer sequence located on the 3'-side of the tag sequence, to form a primer-vector hybrid, where a different identifier tag sequence is used to identify each unique-sequence clone, (4) performing one or more chain extension reactions on each hybrid to form different-length sequencing fragments each terminating with a known base or bases, and (5) combining the different-length sequencing fragments generated from the hybrids, to form the sequencing fragment mixture. The sequencing fragments are then separated on the basis of fragment length under conditions effective to resolve fragments differing in length by a single base, to produce a plurality of resolved size-separated bands. The size-separated bands are collected in separate aliquots, and the identifier tag sequences in each aliquot are amplified to form multiple copies of oligonucleotides complementary to the identifier tag sequences, and optionally, multiple copies of the identifier tag sequences also. Each amplified aliquot is then contacted with an array of immobilized different-sequence tag probes as above, and from the hybridization pattern formed, a nucleotide sequence for at least one sample fragment is determined.

In practicing the invention using amplifiable tag primers, amplification of tag-primer sequences can be linear or exponential, for example. Linear amplification of tagged primer sequences includes repeated cycles of binding and extending of a second primer which is complementary to the first primer sequence in the sequencing fragments, to generate multiple copies of a sequence complementary to the identifier tag sequence. For exponential amplification, each tagged primer additionally includes a second primer sequence which is located on the 5'-side of the tag sequence in the tagged primer, and the amplifying step includes repeated cycles of binding and extending corresponding third and fourth primers to amplify the identifier tag sequences and their complements. Exponential amplification is preferred for sequencing a very large number of different-sequence sample fragments.

With respect to the above tag-primer embodiment, it is also advantageous to use a plurality of different-sequence cloning vectors to enable the simultaneous creation of sequencing fragments from a plurality of different sample templates (also referred to as a template pool) in a single extension reaction mixture. Thus, in this embodiment, step (1) above is performed on a plurality of separate, different-sequence tag-vectors, each different-sequence tag-vector having (i) a cloning site, (ii) located on the 3'-side of the cloning site, a first vector primer sequence which contains a vector-identifier tag region which is unique for each different-sequence tag-vector, to form a plurality of libraries of different-sequence tag-vectors, step (2) is modified to include isolating at least one clone from each different-sequence tag-vector clone library, and step (3) includes mixing together a clone isolated from each different-sequence tag-vector library before said hybridizing, to form a clone mixture. By this approach, a single tag-primer can be used to generate sequencing fragments from a plurality of different sample fragments in a single primer-extension reaction mixture, thus streamlining template preparation and reducing the number of primer extension reactions. Each sequencing fragment product in the extension reaction mixture contains a tag sequence from the extension tag-primer that identifies the pool of tag-vectors from which the fragment was generated and optionally, the terminating base type(s) of the fragments. Each sequencing fragment product also contains a vector-identifier tag sequence which identifies the vector in which the source sample sequence was cloned. The combination of vector tag and primer tag uniquely identifies the sample fragment to which each sequencing fragment corresponds.

In a second general embodiment, the method of the invention involves the use of a plurality of separate, different-sequence vectors, referred to herein as tag-vectors, each containing a unique identifier tag. Each different-sequence tag-vector includes (i) a cloning site, (ii) located to the 3'-side of the cloning site, an identifier tag which is unique for each different-sequence tag-vector, and (iii) located on the 3'-side of the identifier tag, a first primer region. In practicing this embodiment, polynucleotide sample fragments are inserted or cloned into a plurality of each separate, different-sequence tag-vector, to form a plurality of separate libraries of tag-vector clones. Individual clones are selected from each of at least two such libraries and are combined. The combined clones may then be used to form a sequencing fragment mixture by primer extension, for size-fractionation and sequencing analysis as above.

In a third related embodiment, the invention contemplates the use of different-sequence tag-vectors for use with Maxam-Gilbert-type sequencing as described below.

The hybridization patterns produced on the tag-probe arrays of the invention may be detected by any suitable technique. Preferably, fluorescence detection is employed. Other preferred modes of detection include chemiluminescence detection and the use of radioactive labels.

The invention also includes compositions which are used or produced in the course of practicing the sequencing methods of the invention. Thus, the invention includes a polynucleotide mixture comprising a plurality of primer-tag-primer polynucleotides each comprising a first primer sequence, an identifier tag sequence linked to the 3'-side of the first primer sequence, and a second primer sequence linked to the 3'-side of the tag sequence, wherein the first primer sequences are identical to each other, the identifier tag sequence in each primer-tag-primer polynucleotides differs from the tag sequence in every other primer-tag-primer polynucleotide, and the second primer sequences are identical to each other. The invention also contemplates a sequencing fragment mixture comprising a plurality of different-sequence sequencing fragments derived from a plurality of different sample polynucleotide templates, each different-sequence sequencing fragment containing (1) a template-complement region derived from a selected sample template fragment and having a pre-determined base-type located at the 3'-end of the associated fragment, and (2) at the 5'-end of the fragment, a primer-tag-primer region containing (i) a first primer sequence, (ii) an identifier tag sequence linked to the 3'-side of the first primer sequence, and (iii) a second primer sequence linked to the 3'-side of the tag sequence, wherein the first primer sequences in the sequencing fragments are identical to each other, the second primer sequences in said sequencing fragments are identical to each other, and the identifier tag sequence in each primer-tag-primer region uniquely identifies the sample fragment from which the sequencing fragment was derived, and the sequencing fragment's 3'-terminal base type.

In another aspect, the invention includes a kit for use in sequencing a plurality of polynucleotide sample fragments, which is useful in the sequencing methods described herein. In general, the kit includes a plurality of tag-primers or primer-tag-primers as described herein, and an array of immobilized different-sequence tag probes, each tag probe (1) being capable of hybridizing specifically with one of the identifier tag sequences or a tag sequence complement, and (2) having an addressable location within the array. The kit may also include one or more vectors for cloning a plurality of sample fragments whose sequences are to be determined, and directions for performing a method of the invention.

These and other objects and features of the invention will be more fully apparent when the following detailed description of the invention is read in conjunction with the accompanying drawings.

DETAILED DESCRIPTION OF THE INVENTION

I. Definitions

Figure 1A:
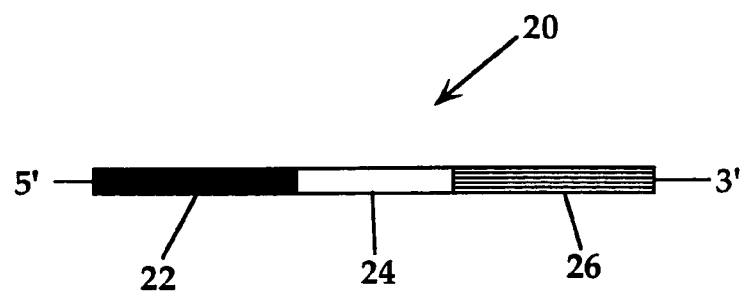
FIGS. 1A and 1B show exemplary tag-primers which may be used in accordance with the invention.

The following terms are intended to have the meanings below unless indicated otherwise.

"Nucleoside" includes natural nucleosides, including ribonucleosides and 2'-deoxyribonucleosides, such as described in Kornberg and Baker (1992), as well as nucleoside analogs having modified bases or sugar backbones, such as described by Scheit (1980) and Uhlman et al. (1990).

A "base" or "base-type" refers to a particular type of nucleosidic base, such as adenine, cytosine, guanine, thymine, uracil, 5-methylcytosine, 5-bromouracil, 2-aminopurine, deoxyinosine, $N^4$-methoxydeoxycytosine, and the like.

"Oligonucleotide" or "polynucleotide" refers to a plurality of nucleoside subunits linked together in a chain, and which are capable of specifically binding to a target polynucleotide by way of Watson-Crick-type hydrogen bonding of base pairs, Hoogsteen or reverse Hoogsteen-type base pairing, or the like. The linkages may be provided by phosphates, phosphonates, phosphoramidates, phosphorothioates, or the like, or by non-phosphate groups as are known in the art, such as peptoid-type linkages utilized in peptide nucleic acids (PNAs) (e.g., Hanvey et al., 1992). The linking groups may be chiral or achiral. The oligonucleotides or polynucleotides may range in length from 2 nucleoside subunits to hundreds or thousands of nucleoside subunits. Preferably, oligonucleotides and polynucleotides are 5 to 100 subunits in length, and more preferably, 5 to 60 subunits in length.

By "specific binding" is meant that a given entity binds exclusively to its intended target under the particular reaction conditions being employed, to the exclusion of all other potential targets. Similarly, "specific hybridization" means that a given entity binds exclusively to its intended complementary target sequence under the particular-hybridization conditions being employed.

"Sequence complement" refers to an oligonucleotide sequence that is complementary to that of a given oligonucleotide.

"Stringent hybridization conditions" refer to conditions which promote hybridization of a given sequence to its sequence complement, without that sequence hybridizing significantly with sequences having a lesser degree of complementarity (i.e., having one or more mismatches). More generally, "stringent hybridization conditions" means conditions which allow hybridization of a given sequence with its intended target(s), without significant hybridization of the sequence with other, different-sequence oligonucleotides which may be present.

By "determining a nucleotide sequence of (or for) a sample fragment" is meant determining a sequence of at least 3 contiguous base subunits in a sample fragment, or alternatively, where sequence information is available for a single base-type, the relative positions of at least 3 subunits of identical base-types occurring in sequential order in the fragment. An example of the latter meaning is a determined sequence "AXXAXA" (5'->3'), where a series of 3 adenine (A) bases are found to be separated by two and then one other base-type in the sample fragment.

II. Method Components

This section describes selected components which are useful in the methods of the invention, including identifier tags, vectors, and tag-probe arrays. A more detailed discussion of the methods of the invention is provided in Section III.

A. Identifier Tags

According to one feature of the invention, there is provided a plurality of tag sequences, or "identifier tags", which are used to uniquely identify the sample fragment or template to which each tag is attached or is otherwise associated with. In addition, the tag sequences may also be used to identify the terminating base-type(s) of the sequencing fragments containing such tags.

As discussed below, different-sequence sample fragments are combined with unique-sequence identifier tags to allow tracking and identification of the sample fragments for sequence determination. In one embodiment, the tags are linked to polymerization primers which are used to generate sequencing fragments via primer extension reactions. In other embodiments, tags are included in cloning vectors which are used to link unique tags to different sequencing fragments.

Preferably, the identifier tags utilized in the invention are composed of unique polynucleotide sequences which (i) have melting temperatures with respect to their corresponding complementary strands that are within a preselected temperature range, and (ii) show substantially no significant cross-hybridization with each other or with the sequence-complements of each other under stringent hybridization conditions. The tags should also not hybridize significantly with any vectors used directly in generating sequencing fragments.

Typically, the sequences of the identifier tags range from 15 to 25 nucleotides in length, although longer or shorter sequences may also be used. For example, an identifier tag can consist of a unique sequence of 10 nucleotides that is flanked on each side by short, non-unique nucleotide sequences (e.g., each 3 to 5 nucleotides in length) that facilitate hybridization to the immobilized tag-probes. The flanking sequences can be the same for all tag-probes to facilitate hybridization, such that discrimination between matched and mismatched pairs depends on the unique tag sequences. Preferably, the unique tag sequences are at least 10 and preferably at least 15 nucleotides in length to facilitate the selection of hybridization conditions that promote adequate binding specificity during hybridization with the tag-probe array. These preferences also apply when both a primer tag sequence and a vector identifier sequence are used, i.e., each tag sequence is preferably at least 10 nucleotides in length, and preferably from 15 to 25 nucleotides in length.

Sequences for the identifier tags which meet the above constraints are selected by generally known methods. Factors which may be considered in determining melting temperature include sequence length, GC content, the relative positions of G/C residues in the sequence with respect to each other, content and position of G residues within the same strand, and the proximity of G/C residues to the 5'- or 3'-terminus of the tag sequence. Preferably, the GC content is greater than 40%. The melting temperature is preferably selected to be between 58 and 70° C., although melting temperatures outside this range may also be suitable.

Candidate identifier tag sequences for use in the invention may also be analyzed to assess the potential for self-hybridization and the formation of internal secondary structure (e.g., hairpin formation). Such characteristics are acceptable in a candidate if they do not occur significantly during hybridization of the identifier tags (or their sequence complements) to the probe array. The possibility of hairpin formation can be further reduced by entirely omitting either G residues or C residues from the tag sequence, although this will have the effect of reducing the total number of sequences from which candidate tag sequences can be selected.

Conveniently, a group of N identifier tag sequences may be generated by computational methods, where N is the number of unique sample sequences desired by the user. An illustrative algorithm for generating such a group is as follows.

First, a tag-probe length, n, or length range $n_1$ to $n_2$, is selected. For the purposes of illustration, n is 20. Next, the GC content is selected to be within a defined range, e.g., 50–55% (10–11 out of 20 nucleotides), or is given a set value, such as 50% (10 out of 20 nucleotides), to constrain the melting temperatures between the tag-probe and its complement to a relatively narrow range. A target melting temperature (e.g., 58° C.) or temperature range (e.g., 58±2° C.) is also selected.

A first tag sequence is then randomly generated, which complies with the preselected GC-content and length constraints, and the melting temperature of the sequence is calculated as above. If the calculated melting temperature is within the preselected range, the sequence is retained as a candidate tag sequence. A second random tag sequence is then generated which complies with the length and GC-content constraints, and its melting temperature is calculated. If the calculated melting temperature is within the preselected target range, the second sequence is added to the list of candidate sequences; otherwise, it is discarded. This process is repeated until a preselected number of candidate tag sequences, e.g., 2N, has been recorded.

The candidate sequences may then be screened for acceptability as tags as follows. The candidate sequences are evaluated to determine their tendencies to (i) hybridize with any already accepted sequence, (ii) hybridize with the sequence complements of the accepted sequences, and (iii) form internal secondary structure. Typically, a melting temperature can be estimated for each of characteristics (i) to (iii) above (e.g., Breslauer et al. (1986); Lowe, 1990). If the melting temperatures for all three characteristics are below a selected threshold (e.g., are at least 10° C. lower than the lower bound of the preselected melting temperatures range), then the candidate sequence is added to the pool of accepted sequences, and the next candidate is evaluated as just described. The process is continued until N acceptable sequences have been found. If the initial number of candidates (e.g., 2N) is not large enough to produce N acceptable sequences, further random sequences may be generated and screened until N acceptable sequences are found.

It is also preferred, but not essential, that the final tag sequences lack significant sequence similarity with regions in the sample fragments and cloning vectors, so that non-specific hybridization of tags can be avoided. Thus, as an optional step, for example, the candidate tag sequences may be screened for sequence similarity with part or all of a database of known sequences, e.g., the GenBank database or the like, with each candidate tag sequence being retained only if the sequence (i) lacks sequence similarity above a selected level, or (ii) would not hybridize with any databank sequence above a selected temperature. In addition, or alternatively, candidate tags and there sequence complements can be screened experimentally against the sample to be sequenced.

Identifier tags may be readily prepared by known synthetic methods, such as described in Caruthers et al. (1989), Beaucage et al. (1992), Stec et al. (1994), Gait (1990), Uhlmann (1990), and the like.

Figure 1B:
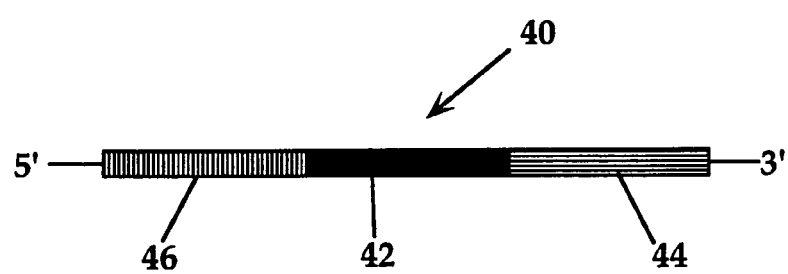

In accordance with one embodiment of the invention, the identifier tags are provided as tag-primers, each comprising an identifier tag sequence and a primer sequence. With reference to FIGS. 1A and 1B, each identifier tag sequence is preferably attached to the 5'-end of a first primer sequence. The tag-primers are particularly useful for forming primer-extended sequencing fragments having a common identifier tag at their 5'-ends which uniquely identifies the sample template being sequenced. The identifier tags may also be used to identify the terminating base-type(s) of selected sequencing fragments, as discussed below.

FIG. 1A shows an exemplary tag-primer 20 containing a unique tag sequence 22, an optional linker region 24, and a primer sequence 26 located to the 3'-side of tag sequence 22 and optional linker region 24. Primer sequence 26 is preferably a "universal" primer sequence for initiating polymerase-mediated primer extension on a conventional cloning vector. Tag sequence 22 may be linked directly to the primer sequence via a phosphorus internucleotide linkage, or via linker region 24 which may be a polynucleotide or non-polynucleotide linker. Primer sequence 26 is also useful as a primer template for preparing multiple copies of the sequence complement of regions 22, 24, and 26 by linear amplification, as discussed further below.

FIG. 1B shows a tag-primer 40 (primer-tag-primer) which includes identifier tag sequence 42, a primer sequence 44 located on the 3'-side of identifier tag sequence 42, and a second primer sequence 46 located on the 5'-side of tag sequence 42. Primer sequences 44 and 46 may be spaced from tag sequence 42 by intervening linkers (not shown). In addition to having the features noted with respect to tag-primer 20 above, tag-primer 40 is amenable to PCR (polymerase chain reaction) amplification of the segment spanning sequences 42, 44 and 46 using repeated cycles of primer binding and primer extension using corresponding third and fourth primers to amplify the identifier tag sequences and their complements. In other words, one of the third and fourth primers contains a sequence complementary to primer sequence 44, and the other contains substantially the same sequence as primer sequence 46 or a portion thereof. An important advantage of primer-tag-primers of the type shown in FIG. 1B is that they allow rapid exponential amplification of the tag identifier in each sequencing fragment without amplifying the sample fragment sequences. This results in an increased quantity of identifier tag with a relative reduction in sample-derived background, so that sensitivity for detecting the identifier tag on a probe-array can be substantially increased.

Figure 2A:
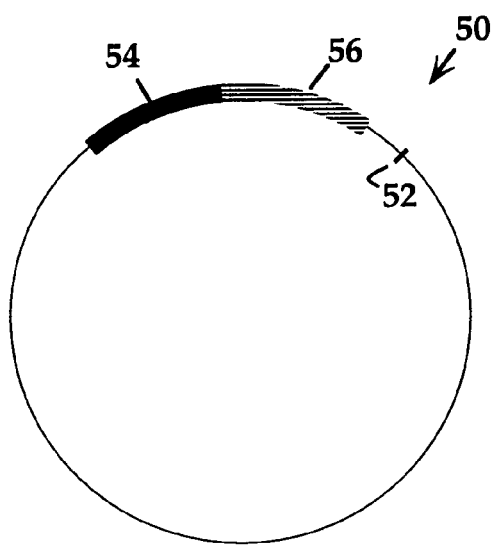
FIGS. 2A and 2B show exemplary vector configurations which may be used in accordance with the invention.

In a further embodiment of the tag-primer and primer-tag-primer approaches discussed above, sample templates can be prepared in a plurality of different-sequence tag-vector libraries to reduce the number of template processing steps prior to the separation and analysis of sequencing fragments. With reference to FIG. 2A as an example, each different-sequence tag-vector 50 contains (i) a cloning site 52, (ii) located on the 3'-side of the cloning site, a universal vector-primer sequence 56 which is the same for all vectors, and (iii) located on the 3'-side of primer sequence 56, a vector-identifier tag sequence 54 that is unique for each different-sequence tag-vector. Each different-sequence tag-vector is used to prepare a separate library of sample-containing clones, such that each sample fragment insert becomes linked with a vector identifier tag region 54 that identifies the corresponding vector library from which the fragment came. A clonal mixture containing a clone isolated from each library can be prepared (also referred to as a template pool), and a mixture of sequencing fragments can be generated using a mixture of primer-tag-primers 40 of the type shown in FIG. 1B, whose primer sequences 44 each contain a region that is complementary to each different vector identifier tag sequence 54. Tag region 42 in primer-tag-primer 40 is used to identify the reaction mixture and/or terminating base type(s) of the sequencing fragments.

Thus, hybridization of the mixture of different primer-tag-primers to the template pool, followed by extension of the hybridized primer-tag-primers with polymerase, produces a mixture of sequencing fragments each containing (i) a 5'-terminal universal primer sequence (46) for subsequent PCR amplification, (ii) a tag sequence (42) that identifies the base terminator type of the fragment and sample source, (iii) a vector identifier tag sequence (a sequence 44 that is complementary to vector sequence 54), and (iv) a 3'-universal primer sequence 44 which is also useful for PCR amplification after the sequencing fragments have been separated by size (length) and collected as same-length aliquots. The tag sequences in the sequencing fragments can be amplified by third and fourth PCR primers, one of which is complementary to the 3'-universal primer sequence 44, and the other of which is identical to the 5'-terminal universal primer sequence (46).

In a related embodiment, vector primer sequence 56 may be omitted from each vector 50, and sequence 54 can be used both as a vector-identifier tag and later as a primer sequence for PCR amplification. Sequencing fragments are prepared as above, except that the resulting sequencing fragments lack a sequence corresponding to the 3'-universal primer sequence 56. After the fragments have been separated and collected on the basis of size, the tag sequences can be amplified using a first primer that is identical to the 5'-universal primer sequence 56 and a mixture of second primers that correspond to the different vector-identifier tags 54. The resultant PCR products contain tag sequences that uniquely identify (i) the source sample fragment and (ii) the terminator base type of the source sequencing fragment. These approaches are illustrated in greater detail in Section III and the Examples below.

It will be appreciated that similar embodiments can be designed using tag-primers in accordance with FIG. 1A, except that exponential PCR amplification of the tag regions after size-separation of the sequencing fragments using a universal primer corresponding to primer sequence 46 is no longer possible.

In accordance with a second general embodiment of the invention, the identifier tags are incorporated in a plurality of cloning vectors, for cloning sample fragments. The vectors contain a universal primer template sequence, and one or more suitable restriction sites for inserting a sample fragment. Each vector also contains a different, unique identifier tag sequence located between the universal primer template sequence and a restriction site.

Figure 2B:
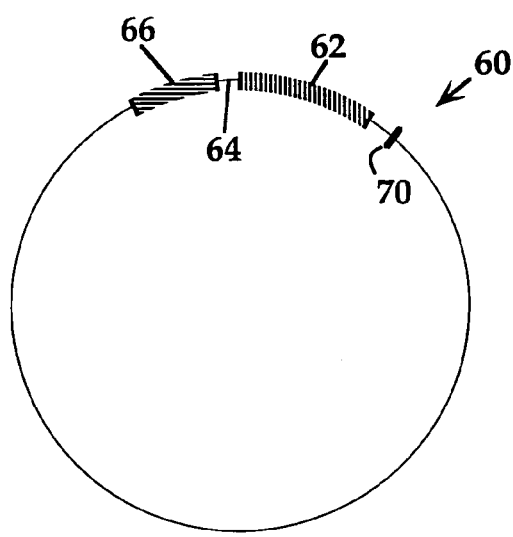

FIG. 2B shows a tag vector 60 which includes cloning site 70; a tag sequence 62 located on the 3'-side of the cloning site; and a primer sequence 66 located on the 3'-side of the identifier tag. Cloning site 70 preferably occurs only once in the vector, for inserting a sample fragment into the vector by ligation. Hybridization of an initiating primer to primer template sequence 66, followed by primer extension, affords sequencing fragments which are complementary to the vector template, each containing sequence complements of the primer template sequence and the identifier tag sequence from the vector. As discussed below, this type of tag vector does not require the use of tag primers.

Methods for preparing vector constructs as described above are well known (see Sambrook, 1989, and Ausubel, 1995).

B. Sequencing Fragments

In general, the identifier tags, primers, and vectors used in the invention are constructed so as to ensure that sequencing fragments are produced which place each identifier tag sufficiently close to a corresponding sample fragment sequence so that the desired level of sequencing information is obtained. Typically, the tag sequence is placed within 40 nucleotide subunits from the sample sequence, and preferably is within thirty subunits from the sample sequence. Similarly, any primer (preferably 25 to 35 nucleotides in length, although primers outside this range may also be used) which is used to amplify a sample sequence or its identifier sequence is also preferably located within 40, and preferably within 20 subunits from the tag or sample sequence. It will be appreciated that the choice of particular tag, primer, and vector configurations is open to considerable flexibility, well within the design choice of one skilled in the art.

The sample polynucleotide fragments to be sequenced may be from any suitable source, whether natural or synthetic. Exemplary samples include genomic DNA, nuclear DNA, cDNA, RNA, or the like, or any subfraction thereof, and may be derived from tissues, cells, microbial organisms, viruses, body fluids such as blood, urine, sweat, ocular fluid, cerebral spinal fluid, and the like. The sample may also be formed by PCR amplification using one or more PCR primers to specifically amplify regions flanked by the primer sequences (e.g., Pardee, 1993). Preferably, the sample has been purified to remove non-polynucleotide materials and any other materials that might interfere with sequencing.

Conveniently, the sample or samples contain polynucleotide fragments within a selected size-range, e.g., 400–2000 nucleotides, to achieve a desired sampling frequency for effective shotgun sequencing. Fragments having selected size ranges may be prepared by standard methods, such as sonication, digestion with endonucleases and exonucleases, chemical degradation, and the like. The size range may be controlled further by subjecting the sample to agarose or polyacrylamide gel electrophoresis, size-exclusion chromatography, or other separation methods, and selecting subfractions having the desired size range.

The different-sequence sample fragments may be provided as separate, same-sequence fragment populations to facilitate linkage with different, unique identifier tags. In a general embodiment, individual same-sequence fragment populations are prepared by ligating the fragments into suitable cloning vectors, propagating the vectors using an appropriate host, and preparing separate colonies or plaques (clones), each containing a sequence derived from a sample fragment which may be the same as, or different from, the fragments contained in the other clones. One or more individual clones are then selected for preparing sequencing fragments as discussed further below.

Exemplary cloning vectors which may be used include phage such as m13 and lambda phage, plasmids such as pUC18 and pUC19, baculoviruses, and the like, modified as necessary to accommodate user preferences. The vectors may additionally contain selection markers, such as ampicillin, streptomycin, and/or tetracycline resistance genes, an origin of replication, transcription terminator sequences downstream of the vector cloning site, and any other conventional feature appropriate for vector propagation.

In a first embodiment for use in preparing sequencing fragments, wherein tag-primers (e.g., FIGS. 1A–1B) and a single cloning vector are employed, the sample fragments are inserted into a plurality of identical cloning vectors by standard ligation techniques, to form a mixture of sequencing vectors each containing a different sample fragment. The mixture of sequencing vectors is plated or otherwise dispersed on a growth-promoting substrate, typically an agar-based solid medium, under dilute conditions such that individual homogeneous clones can be isolated, each containing a different sequencing vector. Typically, a plurality of individual clones (usually still contained in host cells) are removed from the substrate and are each transferred to separate vessels containing a suitable growth medium, to increase the amount of DNA (or RNA) available for sequencing. The sequencing vectors are then isolated from each vessel and kept separate from each other for subsequent use as primer-extension templates.

Sequencing fragments may be generated from each sequencing vector template using any of a number of approaches, depending in part on whether more than one label type is being used for detection. Assuming that only a single label is to be used, each sequencing vector template is divided into four separate aliquots, one for each possible terminating base-type, for conducting primer extension reactions.

In one embodiment, each of the four aliquots for a given vector template is reacted with a different tag-primer, and primer extension is carried out using a DNA polymerase in the presence of four deoxynucleotide triphosphates (dNTPs), with a different dideoxy terminator for each aliquot if the Sanger approach is used. Each reaction mixture produces a ladder of sequencing fragments all terminating with the same base-type, and each having the same identifier tag to indicate both the particular sample fragment and the terminator base type for the sequencing fragments produced in that reaction. Thus, for each different sequencing vector template, the product sequencing fragments contain a total of four different identifier tags for that template.

If the sample fragments are provided as a plurality of different vector libraries prior to hybridization, as discussed with reference to FIG. 2A above, a clone from each library can be mixed together to form a clone mixture (also referred to as a template pool) in which each different vector clone is uniquely identified by its vector-identifier tag sequence (54 in FIG. 2A). The clone mixture can be divided into four aliquots as above for primer extension reactions. Each of the four aliquots is reacted with a plurality of tagged primers that all include (i) a first tag region that is identical among all the primers used in the aliquot, for identifying the terminating base-type of the aliquot reaction mixture, and (ii) a second, vector-tag identifier region for hybridizing to the corresponding vector-identifier tag region in each different vector clone in the aliquot to initiate primer extension. A plurality of such template pools can be prepared from the libraries and can be loaded into separate vessels (up to four vessels per template pool for the four terminator base types) for performing multiple chain extension reactions in parallel. The reaction mixtures may then be mixed together for separation on the basis of fragment length. Each sequencing fragment carries a tag sequence that identifies the source template pool, the particular vector type, and terminator base-type.

In a second general embodiment for preparing sequencing fragments, tag-vectors are employed, such as illustrated in FIG. 2B. The sample fragments are inserted into a plurality of separate, different-sequence tag-vectors to form separate libraries of tag-vector clones. Each library contains vectors all having the same identifier tag but different sample fragment inserts. Each library is then separately plated or otherwise dispersed to produce individually isolable clones. A clone is selected from each of at least two of the plated libraries, and the selected clones are combined and are (optionally) grown together in a growth medium for a selected time, or until a selected density has been obtained, to amplify the amount of clonal material for sequencing. The mixture of sequencing vectors is then isolated from the growth medium for use as primer extension template.

Sequencing fragments may be generated from the sequencing vector mixture using a single universal primer which is effective to initiate primer extension through the sample fragment inserts in the vectors. The primer extension reactions may be conducted together using a single aliquot of the vector mixture if four different labels attached to the 3'-terminator bases are used to distinguish the terminating base-types. Alternatively, when a four-label method is used wherein the labels are carried on the extension primer, the primer extension reactions may be separately conducted in four different aliquots, one for each base-type, which upon completion may be combined for all subsequent processing steps.

It should be noted that when tag-vectors are used in accordance with the second embodiment, primer extension beyond the identifier tag regions of the templates leads to incorporation of tag sequence complement regions near 5'-end regions of the nascent sequencing fragments. These tag sequence complements identify the sample fragments from which the sequencing fragments were derived.

In a third embodiment for use in preparing sequencing fragments, tag-vectors are employed which differ from those in the second embodiment in that the primer sequence located on the 3'-side of the tag sequence is omitted. The tag-vectors in this third embodiment include (i) a cloning site, (ii) on the 3'-side of the cloning site, an identifier tag which is unique for each different-sequence tag-vector, and (iii) flanking the cloning site on one side and the identifier tag on the other side, a pair of restriction sites whose base compositions differ from that of the cloning site, Sample fragments are inserted in the cloning sites of a plurality of separate, different-sequence tag-vectors of the type just described, to form separate libraries of tag-vector clones. As with the second embodiment, each library contains vectors all having the same identifier tag but different sample fragment inserts. Each library is then separately plated or otherwise dispersed to produce individually isolable clones. A clone is selected from each of at least two of the plated libraries, and the selected clones are combined and are (optionally) grown together in a growth medium to amplify the amount of clonal material for sequencing. The mixture of sequencing vectors is then isolated from the growth medium for forming sequencing fragments by the approach of Maxam and Gilbert.

Prior to chemical degradation, the sequencing vector mixture is digested with restriction endonucleases which cleave the two restriction sites flanking the tag sequence and the cloning site of the vectors, so as to excise the sample insert (with tag) from the rest of the vector. Exemplary vector constructs which may be used in this embodiment are described in Heller et al. (1991) and Church (1990; "NoC" vectors).

After the fragments containing the sample inserts have been isolated from the cleavage mixture, they may be labeled, e.g., with $^{32}P$ or other type of label by standard methods (e.g., Church, 1988), for subsequent detection in the array hybridization step. Alternatively, the sample insert mixture may be divided into two to four aliquots to allow labeling with up to four different labels, so that the terminating bases can be determined from the different labels. This allows fragments from the different chemical degradation reactions to be combined and processed together after the degradation reaction have been performed separately.

Irrespective of whether the excised sample inserts are to be labeled, the insert mixture is ultimately divided into four aliquots, each of which is treated with one of the Maxam and Gilbert degradation reagents to produce four sets of sequencing fragments. These sequencing fragments must be kept separate from each other for all subsequent processing steps if only one label type is used, or may be mixed and processed together if more than one label type is used.

Other modifications or combinations of the embodiments above will be readily apparent to one skilled in the art. For example, tag vectors in accordance with the invention may include two unique identifier sequences positioned on either side of the cloning site, for generating sequencing fragments from both ends of a sample fragment insert. Also, vectors may include more than one cloning site, each having one or more unique identifier tag sequences in close proximity for preparing tagged fragments by methods described above.

C. Tag-Probe Arrays

Analysis of each size-separated aliquot is accomplished by contacting each aliquot with an array of immobilized different-sequence tag-probes having distinct, addressable positions in the array. By "addressable" is meant that the location of each different-sequence tag-probe region in the array is known.

The tag-probe arrays are preferably configured as a two-dimensional array of hybridization regions at which different tag-probes have been separately immobilized. The hybridization regions are preferably evenly spaced from one another to facilitate location and scanning of the regions for detection of hybridized tags. Conveniently, the hybridization regions are arranged as a two-dimensional array of rows and columns on the surface of a solid support such as a glass; quartz; silicon; polycarbonate; a metallic material, such as GaAs, copper, or germanium; a polymerized gel, such as crosslinked polyacrylamide; or a membrane, such as nylon, polyvinylidine difluoride (PVDF), or poly-tetrafluoroethylene.

Each tag-probe in the array includes a tag-specific binding moiety which is capable of hybridizing specifically with a sample tag sequence, or tag sequence complement, under stringent binding conditions. Each tag-probe may additionally include (i) additional nucleotides at either end of the tag-specific binding region, e.g., to enhance hybridization with the sample, and/or (ii) one or more linking groups for immobilizing the tag-probe in the array.

Immobilization of the tag-probes within the array is accomplished using any of a variety of suitable methods. Preferably, the tag-probes are immobilized by covalent attachment to an array support. To facilitate covalent attachment, each tag-probe may include one or more linker groups which provide means for covalently attaching the tag-probe to the support. The linker groups may be attached to one or both ends of the tag-specific binding region, or may be attached within the binding region, as appropriate. The linker is typically selected to contain a functional group which is reactive with a suitably reactive group on the array support, using chemistries which are not detrimental to the integrity of the tag-specific binding regions of the tag-probes. Exemplary linking chemistries are disclosed in Barany et al. (1991), and Pon et al. (1988), for example.

Alternatively, non-covalent immobilization methods may be used using ligand-receptor type interactions. For example, the tag-probes may contain covalently attached biotin groups as linker groups, for binding to avidin or streptavidin polypeptides which have been attached to a support (e.g., Barrett, 1996). Linker groups may also be designed to provide a spacer arm which allows the tag-specific binding region to separate from the support, rendering the binding region more accessible to the sample. Exemplary linker groups are described, for example, in Fodor et al. (1995).

Where the array is formed on a solid support, the support may include depressions in the support for holding the deposited tag-probes. Elevated protrusions can also be used, onto which the tag-probes are deposited. In yet another approach, the tag-probes are attached to an array of individual beads attached to a surface, via magnetic force if the beads are magnetic (Albretsen, 1990), or with an adhesive, for example.

A variety of immobilization methods have been described which are adaptable for use in the present invention. In one approach, the tag-probes are synthesized directly on a solid support surface by photolithographic methods such as described in Fodor et al. (1991, 1995). Photoremovable groups are attached to a substrate surface, and light-impermeable masks are used to control the addition of monomers to selected regions of the substrate surface by activating light-exposed regions. Monomer addition to the growing polymer chains in the probe regions is continued using different mask arrangements until the desired, different sequence tag-probes are formed at the desired addressable locations.

The masking method of Fodor et al. may also be modified to accommodate block-polymer synthesis. For example, an array of linker groups (e.g., a polypeptide, or an N-protected aminocaproic acid linked to an aminopropyl group) can be formed on the substrate surface via simultaneous activation of all immobilization regions to form a "carpet" of linker groups. Oligonucleotides encoding the tag-specific binding moiety for each tag-probe are then individually deposited on (or adsorbed to) the substrate surface as liquid drops at selected addressable locations, and are exposed to light or heat as appropriate to couple the binding moieties to the immobilized linker groups, preferably while a sufficient amount of solvent still remains from each drop.

In another approach, the tag-probes are immobilized to a support surface by deposition using an automated small-volume dispenser which deposits each different-sequence tag probe onto a different, pre-determined addressable region. For example, immobilization of polynucleotide probes may be accomplished by robotic deposition on a poly-lysine-coated microscope slide, followed by treatment with succinic anhydride to couple the probes to the polylysine moieties, following the conditions described in Schena et al. (1995) and Shalon (1995).

In another approach, an array is formed on a substrate, such as a glass plate, which is covered with a rectangular array of square pieces of polyacrylamide gel which are separated by stripes of empty glass (Khrapko et al., 1991). A different tag-probe is deposited on each gel piece and is bound thereto by reacting a 3'-terminal dialdehyde on the tag-probe with hydrazide groups on the polyacrylamide gel piece.

Tag-probe arrays in accordance with the invention may also be formed by robotic deposition of tag-probes onto nylon (Khrapko et al., 1991). Following deposition, immobilization of the tag-probes may be facilitated by heat or photoactivation as appropriate.

To reduce the amounts of assay reagents used for tag detection, and to facilitate the sequencing of large numbers of fragment sequences, the arrays are preferably formed as microarrays having probe-region densities of greater than 100 regions/cm$^2$, 300 regions/cm$^2$, $10^3$ regions/cm$^2$, $3 \times 10^3$ regions/cm$^2$, $10^4$ regions/Cm$^2$, $10^5$ regions/cm$^2$, or $10^6$ regions/cm$^2$. In addition, the number of different sequence tag-probes in each probe array is preferably equal to or greater than 10, 20, 50, 100, 200, 500, 1000, 3000, 10,000, 30,000, 100,000, or 300,000.

Figure 3:
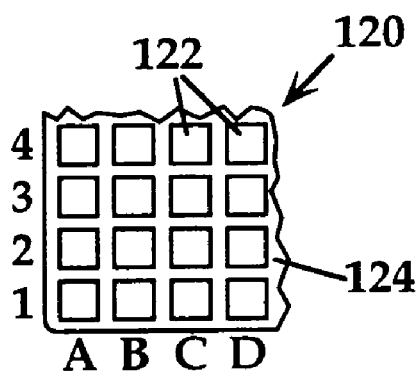
FIG. 3 shows a cut-away portion of an exemplary arrangement for a tag-probe array in accordance with the invention.

FIG. 3 illustrates a cutaway portion of an exemplary tag-probe array in accordance with the invention. Probe array 120 includes a 4×4 array of tag-probe regions 122 arranged in regularly spaced rows and columns on a solid support surface 124. Row labels 1 to 4 and column labels A to D are included in the Figure to illustrate the addressability of the regions. As shown in the FIG. 3, regions 122 are square in shape. However, other shapes, e.g., circles or rectangles, can also be used. More generally, the probe arrays may have any configuration which allows reliable addressing of the tag-probe regions.

III. Sequencing Method

In practicing the present invention, a plurality of sample polynucleotide fragments are used to generate a mixture of sets of different-length sequencing fragments, each set being derived from a different sample fragment. The number of sample fragments which are concurrently sequenced using a hybridization array in accordance with the invention is preferably at least 10, 50, 100, 300, 1000, 3000, 10,000, 100,000 or 300,000.

The sequencing fragments each terminate at a predefined end with a known base or bases, as can be produced by methods of Sanger (1977), Maxam and Gilbert (1977), or any other type of sequencing chemistry which produces the functional equivalent of such fragments. Sequencing fragments are preferably performed by the Sanger approach using dideoxy terminators.

The sequencing fragments in each set contain at least one identifier tag sequence which uniquely identifies the sample fragment to which the sequencing fragments in that set correspond. In a preferred embodiment, up to four different tag sequences are used for each sample fragment, to designate each of the four different terminator base-types in the sequencing fragments generated for that sample fragment. The precise number of tag sequences which identify a particular sample fragment will usually depend on how many label types are used for detection, and on the procedure by which the sequencing fragments are formed.

Two general approaches for practicing the invention may be described as follows. In a first, preferred approach, sample fragments are inserted into identical vectors which are then propagated, separated into individual clones, and isolated. While still separate, the clones are each hybridized with at least one unique tag-primer, to form primer-vector hybrids, which are each reacted under conditions effective to produce a ladder of different length extension products (sequencing fragments), each terminating with a known base-type or base-types. The sequencing fragments from each clone may then be combined to form a mixture for separation into discrete bands on the basis of fragment length, amplification of the tag sequences in each band (a preferred step), and hybridization of the tags to probe arrays (see discussion below and also the Examples).

A useful modification of this first approach is to prepare template pools from a plurality of different vector libraries as discussed above with reference to FIG. 2A, so that sequencing fragments for a plurality of templates can be generated simultaneously in a single reaction chamber, to reduce the number of template preparations and primer extension reactions. This embodiment is illustrated further in Examples 2 and 3.

In a second approach, sample fragments are inserted into each of a plurality of different tagged vectors (see FIG. 2B, for example), which are then propagated separately, to produce a clonal library for each tagged vector. A clone is selected from at least two of the libraries, and the selected clones are mixed together for subsequent primer extension using a universal primer, size fractionation, and probe hybridization.

More generally, sequencing fragments may be generated from a clone mixture by a variety of methods, as discussed above. If only one label type is used for detection, sequencing fragments may be processed together (i.e., separated by size, collected, and hybridized to a plurality of tag probe arrays) in a single aliquot if the tag-primer approach is used, or may be processed together as up to four separate aliquots, one for each class of terminating base-types, if only one identifier tag is associated with each sample fragment. In this respect, the tag-primer method is more advantageous since four different tags can be used for each sample fragment, allowing the sequencing fragments to be processed as a single aliquot using a single label.

Preferably, prior to being separated by length, the sequencing fragments are subjected to a preliminary batch purification step to remove residual reaction components from the fragment mixtures, to enrich the relative concentration of sequencing fragments to be separated. Such reaction components may include a polymerase, nucleotide monomers, and any other reaction reagents. This preliminary purification may be accomplished by agarose gel, anion exchange chromatography, passage through celite or other adsorbent, or the like, such that sequencing fragments in a selected range (e.g., 40 to 240 nucleotides in length) are obtained in purer form.

The sequencing fragments are separated on the basis of size under conditions effective to resolve fragments differing in length by a single base. Such size separations may generally be accomplished by electrophoresis, chromatography, or other technique, provided that single base resolution is obtained.

Conveniently, size-separations are accomplished by capillary electrophoresis (CE) using any of a variety of separation matrices for nucleic acid separations, including covalently crosslinked media (e.g., Huang, 1992) as well as non-covalently crosslinked media (e.g., Menchen, 1994; Grossman, 1994). The size-separated fragments are collected at the outlet of the capillary passageway onto a moving membrane (e.g., Carson, 1992), onto a series of membranes, or preferably into a series of wells, each for a different aliquot. Resolved sequence fragment bands may be monitored by fluorescence or absorption detection, to help coordinate aliquot collection. Where separate collection membranes or wells are used, the collection interval is preferably calibrated to correspond to, at most, one half of the spacing between bands, and preferably, at most, one fourth of the interband spacing, to reduce fragment overlaps. If desired, different pools of sequencing fragments can be loaded into separate capillaries, and aliquots can be collected simultaneously at locked time intervals. Aliquots collected in the same time interval can be mixed together in subsequent steps. Similar considerations apply for collection from chromatography columns.

Alternatively, separation can be accomplished using slab gel electrophoresis, wherein eluting bands are collected onto a moving membrane or in a series of wells under conditions allowing single-base resolution.

Where urea is used in the separation medium, as in standard polyacrylamide gel electrophoresis methods, urea may diffuse from the gel into the collected aliquots, potentially interfering with subsequent enzymatic reactions, or hybridization on the tag-probe arrays. Such urea may be removed by blotting the underlayers of the collection membranes with a dry adsorbent material, to draw urea containing liquid through the membrane, while the sequencing fragments remain on the collection membranes. In another approach, the collection membranes are contacted with an adsorbent containing the enzyme, urease, to convert the urea to ammonia and carbonate. Similarly, a dilute solution of urease may be added if collection wells are used. In yet another approach, the sequencing fragments include cleavable biotin labels which allow the fragments to be bound to streptavidin-coated beads which are then washed to remove the urea, followed by cleavage of the biotin labels to recover the sequencing fragments from the beads.

When sequencing fragments in the collected aliquots contain primer-tag-primer regions, exponential amplification of the identifier tag sequences can be accomplished by polymerase chain reaction (PCR) using a primer pair that is suitable for amplifying the tag regions. The PCR primer pair is reacted with the target sequencing fragments under hybridization conditions which favor annealing of the primers to complementary regions of opposite strands in the target. The reaction mixture is then thermal-cycled through a selected number of rounds (e.g., 20 to 40) of primer extension, denaturation, and primer/target annealing according to well-known polymerase chain reaction (PCR) methods (e.g., Mullis, 1987, and Saiki, 1985). Linear amplification may similarly be performed for primer-tag-primer regions and tag-primers lacking a second, flanking primer by means of a single extension primer for generating tag-complement sequences. Typically, amplification primers are between 10 to 30 nucleotides in length, and are preferably at least 14 nucleotides long to facilitate specific binding of target, although longer or shorter lengths may also be used.

Typically, amplification primers are pre-loaded in reaction vessels along with the standard nucleotide triphosphates, or analogs thereof, for primer extension (e.g., ATP, CTP, GTP, and TTP), and any other appropriate reagents, such as $MgCl_2$ or $MnCl_2$. A thermally stable DNA polymerase, such as "TAQ", "VENT", or the like, may also be pre-loaded in the reaction vessel, or may be mixed with the sample prior to sample loading. Preferably, amplifications are performed simultaneously on a plurality of collected, same-length sequencing bands, using prefabricated microstructures (e.g., capillary tubes or chips) designed for microscale (small-volume) amplifications. Formats for performing such small-volume amplifications are known and have been described in publications by Wilding et al. (1994), Wittwer et al. (1990, 1991), and Northrop et al. (1993), for example. Preferably, the substrate defining the reaction vessels is formed from silicon or glass, although any other material having high thermal conductivity and which is inert towards amplification reagents may also be used.

The collected, preferably amplified, aliquots are contacted with a series of tag-probe arrays, each having an array of addressable tag-probes which correspond to the sample identifier tags, under conditions effective to provide specific hybridization of the tag sequences or tag complements to their corresponding tag-probes, to form a hybridization pattern on each array. Suitable conditions for achieving specific hybridization are well known, and are described in Wetmur (1991), Breslauer et al. (1986), and Schena (1995), for example.

In one embodiment, the sequencing fragments in each aliquot are themselves hybridized to the arrays. In a second, preferred embodiment, the sequencing fragments are amplified linearly or exponentially by iterative cycles of primer-initiated chain extension, to amplify the identifier-tags in the sequencing fragments. In the latter approach, it may be the sequence complements of the identifier tags that hybridize to the array.

Hybridization of tag sequences (or tag sequence complements) to their corresponding tag-probe regions is detected by any means suitable to provide the requisite sensitivity and accuracy. Representative detection methods that may be used include methods based on fluorescence, UV-Vis absorbance, radiolabels, chemiluminescence, spin labels, electrical sensors, and the like, as are known in the art.

To facilitate detection, various methodologies for labeling DNA and constructing labeled oligonucleotides are known in the art. Representative methods can be found in Matthews et al. (1988), Haugland (1992), Keller and Manak (1993), Eckstein (1991); Jablonski (1986); Agrawal (1992); Bergot (1990, 1991); Menchen (1993); Cruickshank (1992); and Urdea (1992).

Hybridization may be detected by scanning the regions of each array simultaneously or serially, depending on the scanning method used. For fluorescence labeling regions may be serially scanned one by one or row by row using a fluorescence microscope apparatus, such as described in Fodor (1995) and Mathies et al. (1992).

Hybridization patterns may also be scanned using a CCD camera (TE/CCD512SF, Princeton Instruments, Trenton, N.J.) with suitable optics (Ploem, 1993), such as described in Yershov et al (1996), or may be imaged by TV monitoring (Khrapko, 1991). For radioactive signals (e.g., $^{32}P$), a phosphorimager device can be used (Johnston et al., 1990; Drmanac et al., 1992). These methods are particularly useful to achieve simultaneous scanning of multiple probe-regions.

Figure 4:
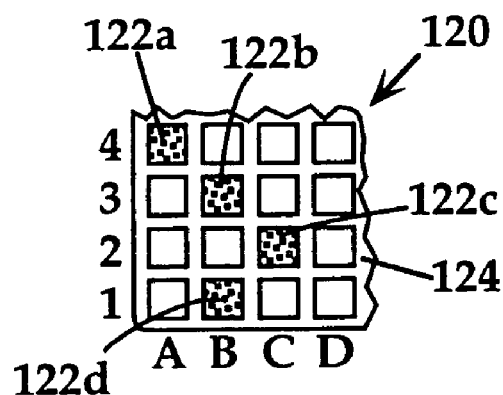
FIG. 4 shows an exemplary hybridization pattern based on the array from FIG. 3.

By way of illustration, FIG. 4 shows a representative hybridization pattern that might be observed on a portion of an array configured as in FIG. 3. Array 120 includes a rectangular array of rows 1–4 and columns A–D of different sequence tag-probe regions 122. Regions 122*a*, 122*b*, 122*c*, and 122*d* at regions 4A, 3B, 2C, and 4B, respectively, indicate regions where sample tags have specifically hybridized. For this example, it is assumed that the four types of Sanger sequencing reactions have been performed separately for each of a plurality of different sample fragments (each having a unique identifier tag), that regions A–D in each row each correspond to a different terminator base-type, i.e., regions A, B, C, and D correspond to base-types A, C, G, and T, respectively, and that each row contains a set of tag-probes specific for a different sample fragment, i.e., row 1 for a fragment 1, row 2 for a fragment 2, and so on.

Given this coding pattern, the hybridization pattern shown in FIG. 4 can be used to infer sequence information at a particular relative location in each sample fragment based on the collection time of the same-size fragment aliquot hybridized to the array. For example, a hybridization signal at region 122*a* means that sample fragment 4 has a base type A at this location in the sample fragment sequence. Similarly, the signal at 122*c* indicates that fragment 2 has a G base-type at this location. If more than one base-type appears to be present at a given sequence position in a sample fragment (e.g., due to band compression which occurred during size-based separation of the sequencing fragments), the correct sequence may be determined by tracing the signal strengths of the four corresponding tag-probe regions as a function of aliquot number or collection time, in much the same way as one determines the sequence of a sample by the time profiles of four fluorescence signals in four-color electrophoretic DNA sequencing.

Similar analysis will apply when two or more different detection labels (e.g., different fluorescent dyes) are used to identify the terminating base types of the fragments.

Figure 5:
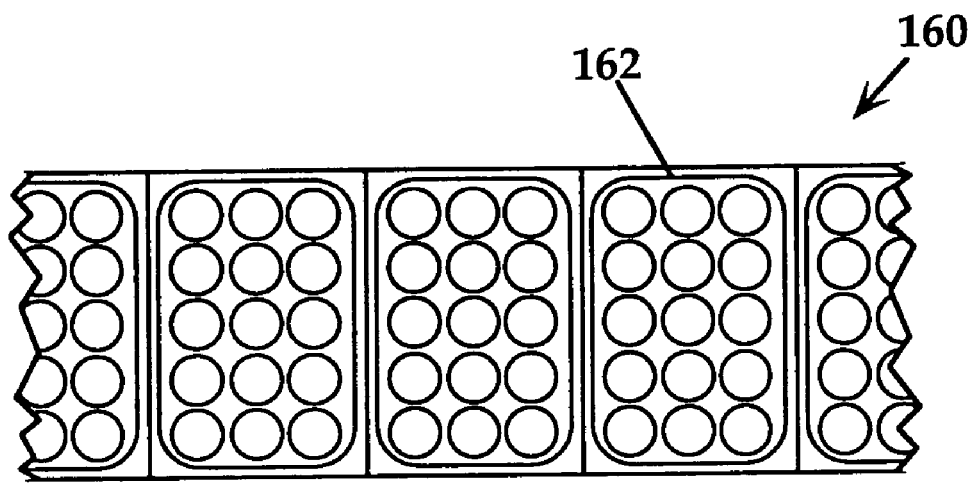
FIG. 5 shows a series of consecutive arrays, each array for analyzing a different size-separated fragment aliquot.

FIG. 5 illustrates a series of identical 3×5 arrays 162 arranged serially along a continuous strip 160. The strip is moved past a scanner apparatus (or vice versa) which records the hybridization signals for each of the tag-probe regions in each array.

The patterns of hybridization on the arrays are preferably analyzed by computer-based methods capable of accomplishing the following functions: (1) recording and correlating hybridized regions with their identifier tags, (2) recording and correlating the terminating base(s) determined for each tag-probe region in each array, and (3) assembling a sequence for each different sample template from the time-profiles of the tag-probe signals associated with that sample template.

The features of the invention will be further appreciated from the following examples which are merely illustrative and are not intended to limit the invention in any way.

EXAMPLE 1

A DNA fragment mixture obtained by sonication of genomic DNA is cloned into a selected vector, such as pUC18. After being cultured, the resultant clonal mixture is plated on agar plates under conditions effective to produce separate colonies. Separate colonies are isolated and cultured. Plasmid DNA from each culture can be isolated by standard methods (e.g., Sambrook et al., 1989), or preferably by automated solid phase preparation methods (Hawkins et al., 1997)

For each isolated plasmid, tag-containing sequencing fragments are generated by the Sanger sequencing method (or any functional equivalent thereof). Four separate sequencing reactions are performed in parallel for each plasmid using four different primer-tag-primers, one for each dideoxy terminator reaction (ddA, ddC, ddG, and ddT, or functional equivalents thereof). With reference to FIG. 1B, each tag-primer includes at its 3'-end, a first "universal" primer region of 20 nucleotides, for hybridizing to the plasmid DNA immediately upstream of the sample insert in the plasmid. Each tag-primer additionally includes a unique tag region of 10 nucleotides linked to the 5'-side of the first universal primer region. The tag region uniquely distinguishes each tag-primer from all others, for identifying the plasmid being sequenced and the base terminator used in the particular sequencing reaction. Finally, each tag-primer additionally includes a second "universal", primer region of 20 nucleotides linked to the 5'-side of the tag region, for later amplification of the primer-tag-primer regions. Thus, in this example, each tag-primer (also referred to as primer-tag-primer) is 50 nucleotides in length.

The sequencing reactions may be conducted in parallel for a large number of different plasmid samples, e.g., for 100, 1000, 10000, 100,000 or more samples. After the sequencing reactions have proceeded for an appropriate time and been stopped, the reaction mixtures are combined to form a mixture of sequencing fragments that are complementary to at least two different sample fragments. Thus, a sequencing fragment mixture prepared from k sample fragments will contain a plurality of sequencing fragments containing different primer-tag-primer sequences as illustrated in Table 1, where $P_{u1}$ and $P_{u2}$ are the first and second universal primer sequences from the primer-tag-primer, $T_n$ represents each tag sequence used for each different sample (four tags per sample to identify A, C, G and T terminator base types), and $S_n$ represent different sample fragments from which the sequencing fragments were derived:

TABLE 1

Correlation Between Tags and Sample Fragments

| Terminal Primer-Tag-Primer | Sample ($S_n$) |
|---|---|
| $P_{u2}$ - $T_1$ (A) - $P_{u1}$ | $S_1$ |
| $P_{u2}$ - $T_2$ (C) - $P_{u1}$ | $S_1$ |
| $P_{u2}$ - $T_3$ (G) - $P_{u1}$ | $S_1$ |
| $P_{u2}$ - $T_4$ (T) - $P_{u1}$ | $S_1$ |
| $P_{u2}$ - $T_5$ (A) - $P_{u1}$ | $S_2$ |
| $P_{u2}$ - $T_6$ (C) - $P_{u1}$ | $S_2$ |
| $P_{u2}$ - $T_7$ (G) - $P_{u1}$ | $S_2$ |
| $P_{u2}$ - $T_8$ (T) - $P_{u1}$ | $S_2$ |
| . . . . . . | . . . . |
| $P_{u2}$ - $T_{4k-3}$ (A) - $P_{u1}$ | $S_k$ |
| $P_{u2}$ - $T_{4k-2}$ (C) - $P_{u1}$ | $S_k$ |
| $P_{u2}$ - $T_{4k-1}$ (G) - $P_{u1}$ | $S_k$ |
| $P_{u2}$ - $T_{4k}$ (T) - $P_{u1}$ | $S_k$ |

The sequencing fragment mixtures and are size-fractionated to isolate fragments within a selected size range, 70–370 nucleotides for the present example. The resultant fragment mixture is then resolved by capillary electrophoresis under conditions effective to provide single-base resolution, i.e., separation of fragments differing in length by a single base. The resolved fragments are collected at the outlet end of the capillary tube into separate receptacles using a computer-controlled fraction collector using collection intervals of about ¼ of the mean inter-base arrival time. Preferably, each fraction is collected onto an adsorbent layer or membrane (e.g., a layer of magnetic beads on a porous membrane near the top of each collection well or vial) that binds the sequencing fragments while allowing non-oligonucleotide materials (e.g., electrolytes and small molecules) to pass through.

For each collected band, PCR amplification of the primer-tag-primer region in the sequencing fragments is performed using a third primer identical to (or having a sequence contained within) the second universal primer sequence in the primer-tag-vector, and using a fourth primer that is complementary to the first universal primer sequence in each primer-tag-vector. Preferably, at least one of the PCR primers includes a detectable label, such as a fluorescent dye, to allow ready detection of the amplified tag sequences when hybridized to a probe array. Upon completion of the PCR step, an amplified band will contain a plurality of amplified primer-tag-primers derived from numerous different sample fragments.

Each amplified mixture is then contacted with one or more probe arrays of the type discussed above, under conditions effective to allow sequence-specific hybridization of the amplified tag sequences (or their amplified complements) to the corresponding probe sequences on the arrays.

In this example, each probe contains a probe region that is complementary to a different selected tag sequence, and which is bordered by an additional 3 nucleotides on each side of the tag complement region, where the bordering nucleotides are complementary to the corresponding universal primer regions (or their complements). Thus, hybridization of the probes to the wrong tag sequences is disfavored by the creation of one or more, and preferably multiple mismatches in the middle portions of mismatched tag/probe duplexes.

The sequence-specific hybridization of an amplified tag sequence to its corresponding immobilized tag probe identifies the terminating base type and source sample fragment to which the tag corresponds.

The probe-arrays are then scanned to determine the hybridization patterns of the hybridized tag fragments for each collected fraction, and the sequence of each template is reconstructed by correlating the observed hybridization signals with fraction collection time.

The advantages of the format used in this example (the use of primer-tag-primers) are at least three-fold. First, unless the degree of parallelism is very small (e.g., less than 100 different template sequences), the number of molecules per fragment species in each fraction may be too low for subsequent hybridization on the probe arrays. This problem is overcome using unique tags bracketed by two universal sequences that afford exponential amplification of the tag sequences before hybridization. Thus, obtaining sequencing information for as many as 50,000 different templates per separation channel can be obtained. Second, the amplification step significantly reduces the possibility of misleading signals that can arise from hybridization of a part of a template sequence to the wrong probe. This problem is avoided because only tagged primers are amplified in the amplification step, not the template sequences. Third, labeling is restricted to copies of the primer-tag-primer regions of the original sequencing fragments. The original sequencing fragments themselves remain unlabeled and therefore do not emit any misleading signals.

EXAMPLE 2

The procedures enumerated in Example 1 are performed with the following modifications.

A DNA fragment mixture is cloned into a plurality of separate, different tag-vectors ($V_k$) of the type shown in FIG. 2A, except that universal primer region 56 is omitted, to form a plurality of vector libraries. Each vector includes a cloning site and a first vector primer sequence ($P_k$) which contains a vector-tag identifier region that is unique for each different-sequence tag-vector $V_k$. A clone from each library is mixed together to form a template pool in which each different vector clone is uniquely identified by the vector-identifier tag region contained in its vector primer sequence $P_k'$. The template pool is divided into four aliquots for performing four separate primer extension reactions, one for each terminator base-type. Each of the four aliquots is reacted with a mixture of primer-tag-primers of the form $P_u$-$T_j$-$P_k$ to generate sequencing fragments from each different sequence clone simultaneously in the same reaction mixture, where $P_u$ is a universal primer sequence for later PCR amplification of the primer-tag-primer region, $T_j$ is a tag sequence for identifying the terminator base-type and sample fragment, and $P_k$ is a vector-specific primer sequence complementary to each unique vector primer sequence $P_k'$. For each vector $V_k$, four different primer-tag-primers of the form $P_u$-$T_j$-$P_k$ are used to generate sequencing fragments in each of four separate aliquots, such that for a given vector $V_k$, four different tags are used (e.g., $T_1$, $T_2$, $T_3$ and $T_4$), one for each terminator base-type, but $P_u$ and $P_k$ are held constant. Thus, a sequencing fragment mixture generated from first and second template pools each formed from k different vector libraries can be represented as shown in Table 2 below.

TABLE 2

Correlation of Primer-Tag-Primers and Sample Numbers for First and Second Template Pool Mixtures

| Terminal Primer-Tag-Primer | Sample ($S_n$) |
|---|---|
| A. First Template Pool Mixture (Samples $S_1$ to $S_k$) | |
| $P_u$ - $T_1$ (A) - $P_1$ | $S_1$ |
| $P_u$ - $T_2$ (C) - $P_1$ | $S_1$ |
| $P_u$ - $T_3$ (G) - $P_1$ | $S_1$ |
| $P_u$ - $T_4$ (T) - $P_1$ | $S_1$ |
| $P_u$ - $T_1$ (A) - $P_2$ | $S_2$ |
| $P_u$ - $T_2$ (C) - $P_2$ | $S_2$ |
| $P_u$ - $T_3$ (G) - $P_2$ | $S_2$ |
| $P_u$ - $T_4$ (T) - $P_2$ | $S_2$ |
| $P_u$ - $T_1$ (A) - $P_k$ | $S_k$ |
| $P_u$ - $T_2$ (C) - $P_k$ | $S_k$ |
| $P_u$ - $T_3$ (G) - $P_k$ | $S_k$ |
| $P_u$ - $T_4$ (T) - $P_k$ | $S_k$ |
| B. Second Template Pool Mixture (Samples $S_{k+1}$ to $S_{2k}$) | |
| $P_u$ - $T_5$ (A) - $P_1$ | $S_{k+1}$ |
| $P_u$ - $T_6$ (C) - $P_1$ | $S_{k+1}$ |
| $P_u$ - $T_7$ (G) - $P_1$ | $S_{k+1}$ |
| $P_u$ - $T_8$ (T) - $P_1$ | $S_{k+1}$ |
| $P_u$ - $T_5$ (A) - $P_2$ | $S_{k+2}$ |
| $P_u$ - $T_6$ (C) - $P_2$ | $S_{k+2}$ |
| $P_u$ - $T_7$ (G) - $P_2$ | $S_{k+2}$ |
| $P_u$ - $T_8$ (T) - $P_2$ | $S_{k+2}$ |
| . . . . . . | . . . . |
| $P_u$ - $T_5$ (A) - $P_k$ | $S_{2k}$ |
| $P_u$ - $T_6$ (C) - $P_k$ | $S_{2k}$ |
| $P_u$ - $T_7$ (G) - $P_k$ | $S_{2k}$ |
| $P_u$ - $T_8$ (G) - $P_k$ | $S_{2k}$ |

After the chain extension reactions are complete, reaction mixtures from a plurality of extended template pools are combined and separated on the basis of length by capillary electrophoresis. Resolved bands are collected and PCR-amplified using a PCR primer mixture comprising universal primer sequence $P_u$ and vector primers $P_1'$ through $P_k'$ (the ' symbol indicates the tag complement of the sequence lacking the ' symbol).

The amplified primer-tag-primer sequences from each band are then hybridized to an array of probes whose sequence are complementary to all possible combinations of $T_j P_k$ to identify the sample fragment (from the $P_k$ component) and terminator base-type (from the $T_j$ component).

EXAMPLE 3

The procedure in Example 2 is modified as follows. First, different tag-vectors $V_k$ include universal primer region 56 as shown in FIG. 2A. Second, the PCR primer mixture comprises a first universal primer $P_u$ (corresponding to sequence 46 in FIG. 1B) and a second universal primer $P_{vec}$ corresponding to sequence 56 in FIG. 2A, instead of vector primers $P_1'$ through $P_k'$.

EXAMPLE 4

In a variation of the format illustrated in Example 2, vector primers $P_k$ and tags $T_j$ can be used in a different manner. A template pool is formed from a plurality of sample vector libraries as in Example 2. Each template pool is divided into four aliquots for each of the four terminator base-types. However, the mixture of primers used to generate sequencing fragments from each template pool differ in that for each $P_k$, a different set of tags $T_j$ is used as illustrated in Table 3 below:

TABLE 3

| Terminal Primer-Tag-Primer | Sample ($S_n$) |
|---|---|
| A. First Template Pool Mixture (Samples $S_1$ to $S_k$) | |
| Pu - $T_1$ (A) - $P_1$ | $S_1$ |
| Pu - $T_2$ (C) - $P_1$ | $S_1$ |
| Pu - $T_3$ (G) - $P_1$ | $S_1$ |
| Pu - $T_4$ (T) - $P_1$ | $S_1$ |
| Pu - $T_5$ (A) - $P_2$ | $S_2$ |
| Pu - $T_6$ (C) - $P_2$ | $S_2$ |
| Pu - $T_7$ (G) - $P_2$ | $S_2$ |
| Pu - $T_8$ (T) - $P_2$ | $S_2$ |
| . . . . . . | . . . . |
| Pu - $T_{4k-3}$ (A) - $P_k$ | $S_k$ |
| Pu - $T_{4k-2}$ (C) - $P_k$ | $S_k$ |
| Pu - $T_{4k-1}$ (G) - $P_k$ | $S_k$ |
| Pu - $T_{4k}$(T) - $P_k$ | $S_k$ |
| B. Second Template Pool Mixture (Samples $S_{k+1}$ to $S_{2k}$) | |
| Pu - $T_{4k+1}$ (A) - $P_1$ | $S_{k+1}$ |
| Pu - $T_{4k+2}$ (C) - $P_1$ | $S_{k+1}$ |
| Pu - $T_{4k+3}$ (G) - $P_1$ | $S_{k+1}$ |
| Pu - $T_{4k+4}$ (T) - $P_1$ | $S_{k+1}$ |
| Pu - $T_{4k+5}$ (A) - $P_2$ | $S_{k+2}$ |
| Pu - $T_{4k+6}$ (C) - $P_2$ | $S_{k+2}$ |
| Pu - $T_{4k+7}$ (G) - $P_2$ | $S_{k+2}$ |
| Pu - $T_{4k+8}$ (T) - $P_2$ | $S_{k+2}$ |
| . . . . . . | . . . . |
| Pu - $T_{8k-3}$ (A) - $P_k$ | $S_{2k}$ |
| Pu - $T_{8k-2}$ (C) - $P_k$ | $S_{2k}$ |
| Pu - $T_{8k-1}$ (G) - $P_k$ | $S_{2k}$ |
| Pu - $T_{8k-(T)}$ - Pk | $S_{2k}$ |

After the sequencing fragments have been formed, a plurality of sequencing fragment mixtures are combined and separated on the basis of length by capillary electrophoresis. Resolved bands are collected and PCR-amplified using a PCR primer mixture comprising universal primer sequence $P_u$ and vector primers $P_1'$ through $P_k'$, as in Example 2. However, the probe-hybridization step differs in that the immobilized probe tags do not need to contain any $P_k$ sequences, since the $T_j$ tag sequences are sufficient to encode each sample fragment and terminator base-type. This format has the advantage of decoupling the sequence compositions of the immobilized probes from the vector identifier sequences, so that the probe array can be used with other vector libraries.

EXAMPLE 5

The procedure in Example 4 is modified as follows. First, different tag-vectors $V_k$ include universal primer region 56 as shown in FIG. 2A. Second, the PCR primer mixture comprises a first universal primer $P_u$ (corresponding to sequence 46 in FIG. 1B) and a second universal primer $P_{vec}$ corresponding to sequence 56 in FIG. 2A, instead of vector primers $P_1'$ through $P_k'$.

Although the invention has been described with respect to particular embodiments, it will be appreciated that various changes and modifications can be made without departing from the invention. All references cited in the present application are hereby incorporated by reference.

The invention claimed is:

1. A method of sequencing in parallel at least one nucleotide of a plurality of polynucleotide sample fragments, the method comprising:
   (a) providing a plurality of polynucleotide sample fragments,
   (b) from said sample fragments, forming a mixture of sequencing fragments, wherein (1) each sequencing fragment terminates at a predefined end with a known base, and (2) each sequencing fragment contains an identifier tag sequence which identifies the sample fragment to which the sequencing fragment corresponds and optionally, the terminating base-type of the fragment, wherein said forming includes the steps of:
      (1) hybridizing to each sample fragment, a tagged primer containing (i) an identifier tag sequence, and (ii) a primer sequence located on the 3'-side of the tag sequence wherein each tagged primer has a primer sequence that is complementary to a unique sample fragment in said plurality of sample fragments, to form a plurality of tagged primer-sample fragment hybrids, where at least one different identifier tag sequence is used to identify each sample fragment,
      (2) performing a chain extension reaction on each hybrid to form sequencing fragments extended by at least one base, and
      (3) combining the sequencing fragments generated from the hybrids, to form a sequencing fragment mixture,
   (c) contacting the sequencing fragment mixture with an array of immobilized different-sequence tag probes, each tag probe (1) being capable of hybridizing specifically with one of said identifier tag sequences, and (2) having an addressable location in said array, where said contacting is conducted under conditions effective to provide specific hybridization of the identifier tag sequences, or tag sequence complements, with the corresponding immobilized tag probes, to form a hybridization pattern on said array, and
   (d) from the hybridization pattern formed, determining a nucleotide sequence for at least one base in at least one sample fragment.

2. The method of claim 1, wherein for each sample fragment to be sequenced there are at least two unique tagged primers, wherein each of the tagged primers has a different tag sequence and a common primer sequence.

3. The method of claim 1, wherein for each sample fragment to be sequenced there are four unique tagged primers, wherein each of the tagged primers has a different tag sequence and a common primer sequence.

4. The method of claim 2, wherein the chain extension reaction of each of the at least two unique tagged primers is done in a separate reaction.

5. The method of claim 1, wherein the chain extension reaction is performed in the presence of chain terminating nucleotides.

6. The method of claim 5, wherein the chain terminating nucleotides are dideoxynucleotides.

7. The method of claim 1, wherein sequencing fragments are labeled with a fluorescent label.

8. The method of claim 7, wherein said fluorescent label is attached to the 5'-end of a sequencing fragment.

9. The method of claim 7, wherein said fluorescent label is attached to the 3'-end of a sequencing fragment.

10. The method of claim 7, wherein a different fluorescent label is used to identify each different terminating base-type.

11. The method of claim 1, wherein sequencing fragments are labeled with a radioactive label.

12. The method of claim 1, wherein each tag primer comprises a common priming sequence located on the 5'-side of the tag sequence.

13. A polynucleotide mixture comprising:
 a plurality of primer-tag-primer polynucleotides each comprising a first primer sequence, an identifier tag sequence linked to the 3'-side of the first primer sequence, a second primer sequence located on the 3'-side of the tag sequence wherein each primer-tag-primer polynucleotide has a second primer sequence that is complementary to a unique sample fragment in a plurality of polynucleotide sample fragments and an additional polynucleotide sequence linked to the 5'-side of the second primer sequence,
 wherein the first primer sequences are identical to each other, the identifier tag sequence in each primer-tag-primer polynucleotides differs from the tag sequence in every other primer-tag-primer polynucleotide and the additional polynucleotide sequences are identical to each other.

* * * * *